United States Patent [19]
Naito et al.

[11] Patent Number: 5,550,095
[45] Date of Patent: Aug. 27, 1996

[54] PROCESS FOR PRODUCING CATALYST USED FOR SYNTHESIS OF METHACRYLIC ACID

[75] Inventors: Hiroyuki Naito; Masato Otani, both of Hiroshima; Motomu Oh-Kita, Tokyo; Toru Kuroda, Hiroshima, all of Japan

[73] Assignee: Mitsubishi Rayon Co., Ltd., Tokyo, Japan

[21] Appl. No.: 331,484

[22] PCT Filed: May 7, 1993

[86] PCT No.: PCT/JP93/00597

§ 371 Date: Nov. 4, 1994

§ 102(e) Date: Nov. 4, 1994

[87] PCT Pub. No.: WO93/23161

PCT Pub. Date: Nov. 25, 1993

[30] Foreign Application Priority Data

May 8, 1993 [JP] Japan .................................. 4-115917

[51] Int. Cl.$^6$ .............................. B01J 27/19; C07C 51/16
[52] U.S. Cl. .......................... 502/211; 502/312; 502/321; 502/353; 562/535
[58] Field of Search .................................. 502/211, 312, 502/321, 353; 562/535

[56] References Cited

U.S. PATENT DOCUMENTS

| | | | |
|---|---|---|---|
| 4,172,809 | 10/1979 | Triki | 252/455 R |
| 5,128,298 | 7/1992 | Schubert et al. | 502/174 |
| 5,173,468 | 12/1992 | Boehning et al. | 502/209 |
| 5,215,952 | 6/1993 | Bielmeier et al. | 502/209 |

FOREIGN PATENT DOCUMENTS

| | | |
|---|---|---|
| 60-48143 | 3/1985 | Japan . |
| 3-167152 | 7/1991 | Japan . |
| 3-238051 | 10/1991 | Japan . |
| 6-15178 | 1/1994 | Japan . |

*Primary Examiner*—Shrive Beck
*Assistant Examiner*—Timothy H. Meeks
*Attorney, Agent, or Firm*—Armstrong, Westerman, Hattori, McLeland & Naughton

[57] ABSTRACT

There is provided a process for efficient production of a solid catalyst usable for synthesis of methacrylic acid from methacrolein which comprises adding a lower alcohol or acetone to a dried product obtained from a mixed solution or aqueous slurry containing at least Mo, P and V as catalyst components and shaping the mixture by extrusion molding.

5 Claims, No Drawings

PROCESS FOR PRODUCING CATALYST USED FOR SYNTHESIS OF METHACRYLIC ACID

TECHNICAL FIELD

The present invention relates to a process for producing a catalyst used for synthesis of methacrylic acid from methacrolein by gas phase catalytic oxidation.

BACKGROUND ART

Hitherto, many proposals have been made on the process for synthesis of methacrylic acid by gas phase catalytic oxidation of methacrolein and on the catalysts used therefor. Especially, since heteropoly-acid type catalysts have been found as catalysts for oxidation of methacrolein, improvement of the catalysts has been proposed in many patents such as, for example, Japanese Patent Kokai (Laid-Open) Nos. 58-96041, 61-7233, 62-153243, 3-238051, etc.

When these catalysts are used in a fixed bed, the catalyst particles must be molded into a suitable size. For the molding of catalysts, it is necessary to employ the conditions most preferable for the properties of the catalyst components per se and the reaction used, and in the case of such a partial oxidation reaction of methacrolein to methacrylic acid as of the present invention, pores inside the molded catalyst are important to obtain the desired product in a high yield. By securing the pores, catalysts excellent in both the activity and the selectivity can be obtained.

However, the heteropoly-acids used in the present invention are inherently poor in moldability and when the conventional pressure molding is employed, a high pressure is required in order to make a molded product having a mechanical strength which can stand industrial use. Therefore, it is difficult to secure the pores in the molded catalysts.

For solving the above problem, mention may be made of the wet molding method. In general, according to the wet molding method, the dry catalyst powder is mixed with an assistant such as a moisturizing component, the resulting mixture is molded into a suitable size, and the molded product is heat treated to remove the moisturizing component. Therefore, this method has the merit that it is easy to secure pores inside the molded catalyst as compared with the pressure molding. Water is normally used as the moisturizing component in the wet molding.

However, since the constituting component of heteropoly-acids dissolves in water, when the wet molding method is applied to the heteropoly-acids and if only water is used as the moisturizing component, there is the tendency that the catalyst active component dissolves away and consequently the inherent performance of the catalyst cannot be exhibited.

As examples of adding a moisturizing component other than water at the time of wet molding, mention may be made of adding lower alcohols such as methyl alcohol and ethyl alcohol as reported in Japanese Patent Kokai (Laid-Open) Nos. 60-48148 and 63-31514. However, these are all supported-type catalysts which comprise a carrier on which a dry catalyst is deposited together with a lower alcohol. Since these supported-type catalysts are smaller in the substantial catalyst amount than molded catalysts prepared by shaping only the catalyst, the reaction temperature must be increased for maintaining a sufficient catalytic activity. As a result, the catalyst life is apt to be adversely affected and further improvement is desired for the use as industrial catalysts.

Furthermore, Japanese Patent Kokai (Laid-Open) No. 1-207137 proposes a process which comprises preparing a concentrated paste containing an alkali metal carbonate, water and an alcohol and extrusion molding the paste. However, this is a process for producing a catalyst carrier used for dimerization of olefins and essentially differs from the method for molding catalyst particles.

Furthermore, in order for controlling the pores inside the molded catalyst, there are reports of adding a polyhydric alcohol such as pyrogallol at the time of preparing the catalyst as in Japanese Patent Kokai (Laid-Open) No. 51-136615 and of adding an organic substance such as polyvinyl alcohol at the time of molding the catalyst, heat treating the molded catalyst and using it as a finished catalyst.

The processes of adding polyhydric alcohols or polyvinyl alcohol suffer from the problems that they lack reproducibility of preparation since decomposition temperatures or removing temperatures of these organic compounds are relatively high and there may occur sintering or reduction of the catalyst due to burning of the organic compounds when they are heat-treated. Thus, further improvement has been desired as a process for the production of industrial catalysts.

Furthermore, since the supported-type catalysts are smaller in substantial catalyst amount than molded catalysts which are prepared by shaping only the catalysts, the reaction temperature must be raised for maintaining a sufficient catalytic activity. As a result, there is the defect that the catalyst life is apt to be adversely affected, and further improvement is desired in the use as industrial catalysts.

DISCLOSURE OF INVENTION

The object of the present invention is to provide a process for producing a catalyst used for synthesis of methacrylic acid from methacrolein.

The present invention relates to a process for producing a catalyst usable for synthesis of methacrylic acid by gas phase catalytic oxidation of methacrolein with molecular oxygen which comprises drying a mixed solution or aqueous slurry containing at least molybdenum, phosphorus and vanadium as effective components for catalyst, mixing the resulting dried product with at least one organic compound selected from the group consisting of methyl alcohol, ethyl alcohol, propyl alcohol, butyl alcohol and acetone, and extrusion molding the mixture.

BEST MODE FOR CARRYING OUT THE INVENTION

According to the present invention, after a mixed solution or aqueous slurry containing catalyst components is prepared, most of water is removed therefrom and the residue is dried to obtain a dry catalyst. In the present invention, it is important that the thus obtained dry catalyst is mixed with at least one organic compound selected from the group consisting of methyl alcohol, ethyl alcohol, n- or iso-propyl alcohol (hereinafter referred to as merely "propyl alcohol"), n-, iso- or tert-butyl alcohol (hereinafter referred to as merely "butyl alcohol") and acetone and the mixture is molded by extrusion. The organic compound-containing molded catalyst obtained by mixing with the organic compound such as methyl alcohol and extrusion molding the mixture is dried and then heat-treated to obtain a catalyst having sufficient pores and having excellent catalytic activity with good reproducibility. In practice of the present invention, butyl alcohol is preferred among the above-mentioned organic compounds.

Amount of the organic compound such as methyl alcohol to be mixed with the dry catalyst in the present invention is not particularly critical and the compound may be added in an optional amount depending on the purpose, but the amount is preferably 5–50% by weight, especially preferably 10–30% by weight based on the weight of the dry catalyst. When the amount is less than 5% by weight or more than 50% by weight, the mixture is inferior in moldability in extrusion molding and is not suitable as industrial catalysts. Furthermore, in the present invention, a small amount (several percent by weight) of water may be added in addition to the above-mentioned organic compounds and the object of the present invention can be attained.

At the time of mixing the dry catalyst with the organic compound such as methyl alcohol, there may further be added known inorganic additives such as talc and inorganic fibers.

In the present invention, the method of extrusion molding the mixture of the dry catalyst and the organic compound such as methyl alcohol and the shape of the product are not particularly limited and the mixture can be molded into any shapes such as ring, column, star and the like using a general powder extrusion molding machine.

The thus obtained extrusion molded catalyst is then dried and heat-treated. In the present invention, these treating conditions are not particularly limited and known treating conditions can be applied. Usually, a temperature of 60°–150° C. can be employed as a drying condition and a temperature of 300°–500° C. can be employed as a heat-treating condition.

According to the present invention, a catalyst having the composition represented by the following formula can be advantageously produced:

$$P_a Mo_b V_c Cu_d X_e Y_f Z_g O_h$$

(wherein P, Mo, V, Cu and O represent phosphorus, molybdenum, vanadium, copper and oxygen, respectively, X represents at least one element selected from the group consisting of antimony, bismuth, arsenic, germanium, zirconium, tellurium, silver, selenium, silicon, tungsten and boron, Y represents at least one element selected from the group consisting of iron, zinc, chromium, magnesium, tantalum, cobalt, manganese, barium, gallium, cerium and lanthanum, Z represents at least one element selected from the group consisting of potassium, rubidium, cesium and thallium, a, b, c, d, e, f, g and h represent the atomic ratio of each element and when b is 12, a is 0.5–3, c is 0.01–3, d is 0.01–2, e is 0–3, f is 0–3 and g is 0.01–3, and h is the number of oxygen atom necessary to satisfy the valence of each component).

The process for producing the catalyst having the composition used in the present invention need not be limited to a specific process and conventionally well known various processes such as a process of evaporation to dryness, a process of precipitation, a process of mixing of oxides and the like can be used as far as the components are not so unevenly distributed.

As starting materials for the catalyst components, there may be used oxides, nitrates, carbonates, ammonium salts, halides, etc. of the elements in combination. For example, ammonium paramolybdate, molybdenum trioxide, molybdenum chloride, etc. can be used as the molybdenum starting materials and ammonium metavanadate, vanadium pentoxide, vanadium chloride, etc. can be used as the vanadium starting materials.

In utilizing the catalyst obtained in the present invention, the concentration of methacrolein in the starting material gas can be varied over a wide range, but 1–20 vol % is suitable and 3–10 vol % is especially preferred. The starting methacrolein may contain a small amount of impurities such as water and lower saturated aldehydes and these impurities do not exert substantial influence upon the reaction.

It is economical to use air as an oxygen source in effecting the catalytic oxidation, but, if necessary, air enriched with pure oxygen can also be used. The oxygen concentration in the starting material gas is specified by the molar ratio to methacrolein and this is preferably 0.3–4, especially preferably 0.4–2.5. The starting material gas may be diluted with addition of inert gas such as nitrogen, steam or carbon dioxide.

Reaction pressure is suitably from atmospheric pressure to several atm. Reaction temperature can be chosen in the range of 200°–450° C. and 220°–400° C. is especially preferred.

When the catalyst obtained by the present invention is used for the production of methacrylic acid by gas phase catalytic oxidation of methacrolein, the advantageous effect that methacrylic acid can be produced in a high yield is obtained.

EXAMPLES

The process for producing the catalysts according to the present invention and reaction examples of using the catalysts will be explained in detail below.

The reaction rate of methacrolein and the selectivity for methacrylic acid produced in Examples and Comparative Examples are defined as follows.

$$\text{Reaction rate of methacrolein (\%)} = \frac{\text{Mol number of the reacted methacrolein}}{\text{Mol number of the fed methacrolein}} \times 100$$

$$\text{Selectivity for methacrylic acid (\%)} = \frac{\text{Mol number of the produced methacrylic acid}}{\text{Mol number of the reacted methacrolein}} \times 100$$

Part in the following examples and comparative examples is by weight unless otherwise notified and the analysis was conducted by gas chromatography.

Example 1

The procedure of Example 10 of Japanese Patent Kokai (Laid-Open) No. 3-167152 was followed. That is, 100 parts of ammonium paramolybdate, 4.42 parts of ammonium metavanadate and 6.96 parts of rubidium nitrate were dissolved in 300 parts of pure water. Thereto were added a solution prepared by dissolving 8.16 parts of 85% phosphoric acid in 10 parts of pure water and further added a solution prepared by dissolving 1.11 part of 60% arsenic acid in 20 parts of pure water, a solution prepared by dissolving 0.61 part of magnesium nitrate in 20 parts of pure water, a solution prepared by dissolving 0.24 part of chromium oxide in 20 parts of pure water and a solution prepared by dissolving 3.24 parts of gallium nitrate (Ga content: 20.3%) in 20 parts of pure water. The resulting mixture was heated to 95° C. with stirring. Then, thereto was added a solution prepared by dissolving 1.14 parts of copper nitrate in 30 parts of pure water, thereby obtaining a mixed solution containing catalyst components. The solution was subjected to evaporation to dryness and the resulting solid was dried at 130° C. for 16 hours.

100 parts of the resultant dry powder was mixed with 20 parts of ethyl alcohol and the mixture was molded into a ring of 5 mm in outer diameter, 2 mm in inner diameter and 5 mm in average length by an extrusion molding machine. This extrusion-molded product containing ethyl alcohol was dried at 130° C. for 6 hours and then heat-treated at 380° C. for 5 hours under passing of air to obtain a catalyst.

Composition of the elements of the resulting catalyst except for oxygen (same in the following) was $P_{1.5}Mo_{12}Cu_{0.1}V_{0.8}Ga_{0.2}As_{0.1}Mg_{0.05}Cr_{0.05}Rb_1$.

The resulting catalyst was packed in a reaction tube and a mixed gas comprising 5% of methacrolein, 10% of oxygen, 30% of steam and 55% of nitrogen (vol %) was passed therethrough at a reaction temperature of 270° C. for a contacting time of 3.6 seconds. The product was collected and analyzed by gas chromatography to give a reaction rate of methacrolein of 92.8% and a selectivity for methacrylic acid of 89.0%.

Comparative Example 1

The extrusion molding and reaction were conducted in the same manner as in Example 1 except that n-octyl alcohol was used in place of the ethyl alcohol mixed with 100 parts of the dry powder. As a result, the reaction rate of methacrolein was 90.5% and the selectivity for methacrylic acid was 85.6%.

Comparative Example 2

The extrusion molding was conducted in the same manner as in Example 1 except that amount of the ethyl alcohol mixed with 100 parts of the dry powder was 3.5 parts. Moldability was considerably poor and the desired molded catalyst could not be obtained.

Comparative Example 3

The extrusion molding was conducted in the same manner as in Example 1 except that amount of the ethyl alcohol mixed with 100 parts of the dry powder was 110 parts. Moldability was considerably poor and it was difficult to retain the shape of the molded product, and the desired molded catalyst could not be obtained.

Example 2

The extrusion molding and reaction were carried out in the same manner as in Example 1 except that 24.5 parts of acetone was used in place of 20 parts of the ethyl alcohol mixed with 100 parts of the dry powder. Results of the reaction are shown in Table 1.

Comparative Example 4

The extrusion molding and reaction were carried out in the same manner as in Example 2 except that 20 parts of glycerin was used in place of 24.5 parts of the acetone mixed with 100 parts of the dry powder. Results of the reaction are shown in Table 1.

Example 3

The reaction was carried out under the same conditions as in Example 1 except that 18.5 parts of isobutyl alcohol was used in place of 20 parts of the ethyl alcohol mixed with 100 parts of the dry powder, furthermore, 3 parts of inorganic fibers having an average length of 200 μm were added and the mixture was molded into a ring of 5.5 mm in outer diameter, 2 mm in inner diameter and 4 mm in average length by an extrusion molding machine. Results of the reaction are shown in Table 1.

Example 4

The extrusion molding and reaction were carried out in the same manner as in Example 3 except that 22 parts of methyl alcohol was used in place of 18.5 parts of the isobutyl alcohol mixed with 100 parts of the dry powder. Results of the reaction are shown in Table 1.

Example 5

The procedure of Example 6 of Japanese Patent Kokai (Laid-Open) No.3-238051 was followed. That is, 100 parts of ammonium paramolybdate, 4.42 parts of ammonium metavanadate, 3.34 parts of potassium nitrate and 3.68 parts of cesium nitrate were dissolved in 300 parts of pure water. Thereto were added with stirring a solution prepared by dissolving 8.16 parts of 85% phosphoric acid in 10 parts of pure water and further added a solution prepared by dissolving 2.22 parts of 60% arsenic acid in 20 parts of pure water, a solution prepared by dissolving 4.10 parts of cerium nitrate in 20 parts of pure water and a solution prepared by dissolving 1.14 parts of copper nitrate in 20 parts of pure water. Then, to the resulting mixed solution was added a homogeneous bismuth nitrate solution obtained by adding 7.0 parts of 60% nitric acid and 35 parts of pure water to 6.86 parts of bismuth nitrate, followed by heating to 95° C. Then, to the mixed solution was added 2.06 parts of antimony trioxide to prepare a mixed solution containing catalyst components. The resulting solution was subjected to evaporation to dryness and the resulting solid was dried at 130° C. for 16 hours.

100 parts of the resultant dry powder was mixed with 10 parts of ethyl alcohol and 12 parts of isopropyl alcohol and the mixture was molded into a four-leafed ring of 6 mm in the longest outer diameter, 5 mm in the shortest outer diameter, 2 mm in inner diameter and 5 mm in average length by an extrusion molding machine. This extrusion-molded product containing ethyl alcohol and isopropyl alcohol was dried at 130° C. for 6 hours and then heat-treated at 380° C. for 5 hours under passing of air.

Composition of the elements of the thus obtained catalyst was $P_{1.5}Mo_{12}V_{0.8}Cu_{0.1}K_{0.7}Cs_{0.4}Bi_{0.3}Sb_{0.3}Ce_{0.2}As_{0.2}$.

The reaction was carried out using this catalyst under the same conditions as in Example 1 except that the reaction temperature was 290° C. Results of the reaction are shown in Table 1.

Example 6

The procedure of Example 12 of Japanese Patent Kokai (Laid-Open) No.3-167152 was followed. That is, 100 parts of ammonium paramolybdate, 2.76 parts of ammonium metavanadate and 9.20 parts of cesium nitrate were dissolved in 300 parts of pure water. Thereto were added a solution prepared by dissolving 10.88 parts of 85% phosphoric acid in 15 parts of pure water and further added, a solution prepared by dissolving 1.08 parts of telluric acid in 30 parts of pure water, a solution prepared by dissolving 0.40 part of silver nitrate in 30 parts of pure water, a solution prepared by dissolving 6.14 parts of cerium nitrate in 20 parts of pure water and a solution prepared by dissolving 4.86 parts of gallium nitrate (Ga content: 20.3%) in 30 parts of pure water. The resulting mixture was heated to 95° C.

with stirring. Then, thereto was added a solution prepared by dissolving 1.14 parts of copper nitrate in 30 parts of pure water, thereby to prepare a mixed solution containing catalyst components. The solution was subjected to evaporation to dryness and the resulting solid was dried at 130° C. for 16 hours.

100 parts of the resultant dry powder was mixed with 10 parts of isobutyl alcohol, 10 parts of acetone and 5 parts of inorganic fibers and the obtained mixture was molded into a ring of 5 mm in outer diameter, 2 mm in inner diameter and 5 mm in average length by an extrusion molding machine. This extrusion-molded product containing isobutyl alcohol and acetone was dried at 130° C. for 6 hours and then heat-treated at 380° C. for 5 hours under passing of air to obtain the desired catalyst.

Composition of the elements of the thus obtained catalyst was $P_2Mo_{12}Cu_{0.1}V_{0.5}Ga_{0.3}Te_{0.1}Ag_{0.05}Ce_{0.3}Cs_1$.

The reaction was carried out using this catalyst under the same conditions as in Example 1. Results of the reaction are also shown in Table 1.

TABLE 1

|  | Reaction rate of methacrolein (%) | Selectivity for methacrylic acid (%) |
| --- | --- | --- |
| Example 2 | 92.6 | 89.5 |
| Comparative Example 4 | 89.9 | 86.5 |
| Example 3 | 92.8 | 88.5 |
| Example 4 | 93.1 | 88.3 |
| Example 5 | 91.5 | 88.8 |
| Example 6 | 92.4 | 88.8 |

Comparative Example 5

The extrusion molding and the reaction were carried out in the same manner as in Example 5 except that 20 parts of water was used in place of 10 parts of ethyl alcohol and 12 parts of isopropyl alcohol which were mixed with 100 parts of dried powder. As a result, the methacrolein reaction rate was 90.5% and the methacrylic acid selectivity was 84.5%. Thus, the selectivity decreased.

Industrial Applicability

According to the present invention, extrusion-molding of catalyst is easy and catalysts of various shapes depending on the purposes can be obtained in a high efficiency.

We claim:

1. A process for producing a catalyst for synthesis of methacrylic acid by gas phase catalytic oxidation of methacrolein with molecular oxygen which comprises drying a mixed solution or aqueous slurry of catalytically active material comprising at least molybdenum, phosphorous and vanadium, mixing the resulting dried product with at least one organic compound selected from the group consisting of methyl alcohol, ethyl alcohol, propyl alcohol, butyl alcohol and acetone and molding the mixture by extrusion.

2. A process for producing a catalyst usable for synthesis of methacrylic acid according to claim 1 wherein the organic compound is butyl alcohol.

3. A process for producing a catalyst usable for synthesis of methacrylic acid according to claim 1 wherein the organic compound is used in an amount of 5–50% by weight based on the weight of the dried catalyst.

4. A process for producing a catalyst usable for synthesis of methacrylic acid according to claim 1 wherein the organic compound is used in an amount of 10–30% by weight based on the weight of the dried catalyst.

5. A process for producing methacrylic acid, characterized by synthesizing methacrylic acid by gas phase catalytic oxidation of methacrolein with molecular oxygen using the catalyst obtained by the process of claim 1, 2, 3 or 4.

\* \* \* \* \*